United States Patent [19]

West

[11] Patent Number: 4,861,984

[45] Date of Patent: Aug. 29, 1989

[54] SURFACE INSPECTION OR RANGING APPARATUS WITH IMAGE DEROTATION

[75] Inventor: Robert N. West, Chislehurst, United Kingdom

[73] Assignee: Sira Limited, Kent, United Kingdom

[21] Appl. No.: 116,314

[22] Filed: Nov. 4, 1987

[30] Foreign Application Priority Data

Nov. 10, 1986 [GB] United Kingdom ............... 8626812

[51] Int. Cl.$^4$ .............................................. H01J 3/14
[52] U.S. Cl. ..................................... 250/236; 356/241
[58] Field of Search ............... 356/341; 250/234, 235, 250/236, 216; 350/286, 287, 6.5

[56] References Cited

U.S. PATENT DOCUMENTS

| 4,440,496 | 4/1984 | Milana ................................. 356/241 |
| 4,557,598 | 12/1985 | Ono et al. ........................... 356/241 |
| 4,642,700 | 2/1987 | Ohta et al. .......................... 250/236 |
| 4,717,823 | 1/1988 | Steimel et al. ..................... 250/236 |

Primary Examiner—David C. Nelms
Attorney, Agent, or Firm—Sughrue, Mion, Zinn, Macpeak & Seas

[57] ABSTRACT

Apparatus for measuring surface defects or the distance from the apparatus to a surface comprising means (37,38,43,44) for passing a beam (48) of light to the surface (12) at an angle other than normal, means (51) for viewing the area (47) of the surface (12) illuminated by the beam (48) and means (53-60) for measuring the movement of the illuminated area (47) whereby the measure the position of the illuminated area (47), means (17) being provided to rotate the apparatus and means (53) being provided to derotate the image of the illuminated area so as to enable, for example, the interior of cylinders (10) to be inspected.

12 Claims, 4 Drawing Sheets

SURFACE INSPECTION OR RANGING APPARATUS WITH IMAGE DEROTATION

The present invention relates to a surface inspection or ranging apparatus.

According to one aspect the apparatus is for inspecting surface defects in, for example, a metal surface; in another aspect the apparatus may be used to inspect surface defects in the surface of a hollow cylinder; in another aspect the invention may be used to measure the diameter of the hollow cylinder, or its ovality or its straightness; in another aspect the invention may be used to inspect the finish of a surface; and in a further aspect the apparatus of the invention may be used to measure the honing mark cross hatch angle of a honed surface.

The apparatus will be described in particular with reference to inspecting and ranging the surface of a cylinder bore of an engine block, but apparatus of the invention may be used to inspect or range other surfaces, for example surfaces of hollow parts or exterior surfaces which may be flat or otherwise.

The present invention provides apparatus for measuring surface defects or the distance from the apparatus to a surface comprising first optical means for passing a beam of radiation to the surface at an angle other than normal, second optical means for viewing the area of the surface illuminated by the beam and means for measuring the movement of an image of said illuminated area with respect to the optical axis of the second optical means whereby to measure the position of the illuminated area characterised by means to relatively rotate the optical axis of the first optical means and the surface so that the illuminated area is moved across the surface and means is provided to derotate the image of the illuminated area caused by said relative rotation.

Reducing the cross sectional size of the beam allows one to measure smaller defects. In a preferred arrangement, the cross sectional size of the beam at the surface is 5 microns.

In a preferred arrangement the optical axis of the second optical means is at right angles to the optical axis of the first optical means whereby, if the illuminated area is at the focus of the second optical means, movement of the illuminated area will be in the focal plane of the second optical means.

For measurement of the diameter of a cylinder, the rotational means is adapted to relatively rotate the optical axis of the first optical means and means is provided to move the optical axis parallel to the axis of the cylinder so that the illuminated area is moved around the circumference of the cylinder in a continous helix scan.

In another arrangement, to measure the honing mark cross hatch angle optical means is provided for passing a beam of radiation at the surface, and further optical means is provided to examine the cross section of the radiation reflected from the surface. In practice, if, for example, the surface is illuminated by a beam of circular cross section, the honing mark cross hatch angle shows up as a star-like diffraction pattern in which the arms of the star correspond with the fine scratches caused by the honing and thus the cross hatch angle is measured by measuring the angle between these arms. Means is provided to determine the shape of the cross-section of the beam which comprises means for measuring the angular disposition of the arms with respect to each other.

Through the specification we will refer to "optical" and like expressions. It should be understood that the invention is not restricted to apparatus using radiation of optical (visible) wavelengths but radiation of other wavelengths may be used including infra-red, ultra-violet, x-ray and electron beams where necessary.

Preferred embodiments of the invention will now be described by way of example only with reference to the accompanying drawings, in which.

Figure 1:
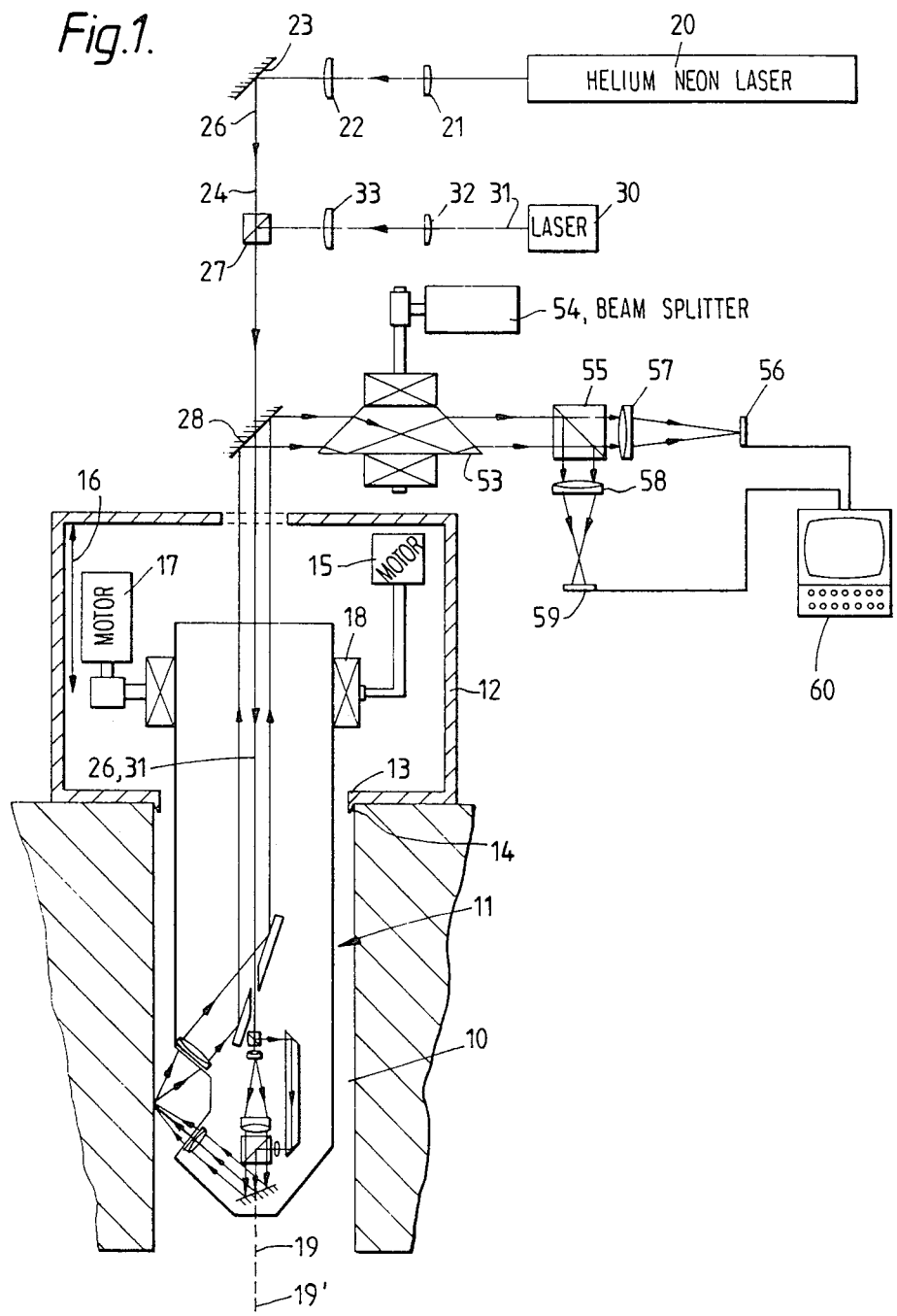
FIG. 1 is a diagramatic section of a first embodiment of the invention.

The apparatus of the figures is specifically designed for inspecting the surface of the wall 10' of a cylinder bore 10 having an axis 19' which cylinder bore 10 may be the cylinder bore of an internal combustion engine. Such a cylinder bore 10 is conventionally provided in a cast engine block, and is bored by means of a rotary tool; after boring the bore is honed by a finishing tool. In honing, the surface is finished by means of a light abrasive honing tool which rotates and passes down and back up the cylinder bore 10. It leaves on the surface of the cylinder bore wall a series of fine helical scratches formed as the tool passes down and back up the cylinder bore.

The apparatus for inspecting and ranging the surface of the cylinder bore 10 comprises a probe 11 mounted within the cylinder bore 10. The probe 11 is mounted within a housing 12, the housing 12 including an annular locating portion 13 which acurately locates with the top rim 14 of the cylinder bore 10.

The probe 11 is mounted within the housing 12 in such a manner as to be moveable up and down within the housing 12 by motor means 15 the movement being indicated by the arrow 16. The probe 11 is also mounted to rotate within the housing 12 by means of very accurate bearings indicated at 18 the bearings 18 being such that the lower end of the probe 11 rotates accurately about the axis 19 of the probe to an accuracy of greater than ±0.25 minute of arc. The probe 11 may be rotated with respect to the housing 12 by means of a motor 17.

The optical components comprise a Helium Neon laser 20 providing a beam 26 of 633 nm wavelength; the beam 26 is shaped by means of collimating lenses 21,22 and is reflected by means of plane mirror 23 onto the main optical axis of the apparatus 24. The optical axis 24 corresponds with the axis 19 of the probe. The beam 26 passes through a beam combiner 27 through a central aperture in a plane mirror 28 and down through the probe 11.

A second laser 30 provides a beam 31 of 820 nm wavelength (infra red); the beam 31 is collimated by lenses 32,33 and is passed to the beam combiner 27 where it is combined with the beam 26 and passes down along the optical axis 24 to the probe 11.

Figure 2:
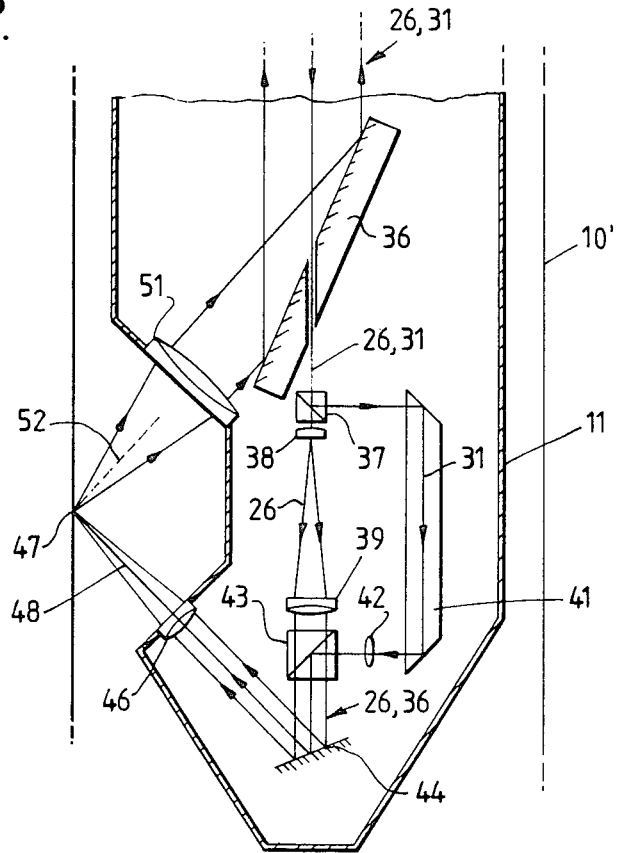
FIG. 2 is an enlargement of part of FIG. 1.

Details of the optical components at the lower end of the probe 11 are shown in enlarged size in FIG. 2. The combined beam 26,31 passes through a central aperture in a plane mirror 36 to a beam splitter 37.

The beam splitter 37 separates the two beam components 26,31, the infra red laser beam 31 being directed at right angles into an off-set path whilst the HeNe laser beam 26 passes on along the optical axis 24 to be expanded by two doublet lenses 38,39 acting as a telescope. The infra red beam 31 is directed around the telescope 38,39 by a prism 41.

After leaving the reflecting prism 41 the infra red beam 31 passes through a lens 42 and is then recombined with the beam 26 in a beam combiner 43. The combined beam 26,31 is then reflected by a plane mirror 44 towards a doublet lens 46 which focuses the HeNe laser beam 26 down to microns sized, typically 5 micron diameter spot 47 on the wall 10' of the cylinder bore 10.

On the other hand, the infra red laser beam 31 is shaped by the doublet lens 46 and lens 43 to be a collimated beam of approximately 1 mm diameter at the cylinder wall 10'.

As will be clear from FIGS. 1 and 2 the optical axis 48 of the lens 46 and hence the path of the combined beams 26,31 strikes the wall 10' at 45°.

The reflected combined beam 26,31 is collected by a doublet lens 51. By choosing the angle between the optical axis 48 and the wall 10' to be 45°, the reflected beam axis 52 and wall 10' are also at 45°. The effect of this is that the optical axis 48 is at right angles to the axis 52 of the lens 51.

The doublet lens 51 collimates the reflected combined beam 26,31 and this is reflected out of the probe 11 by the plane mirror 36.

At the plane mirror 28 most of the light will be directed towards a dove prism 53 mounted so as to be rotatable about its axis by a motor 54. After passing through the dove prism 53 the combined beam 26,31 passes to a beam splitter 54 which separates the two beams, the HeNe laser beam 26 passing through the beam splitter 54 to be focused onto a position sensitive photo detector 56 such as a Sitech IL 2.5. The lens 51 and focusing lens 57 between the beam splitter 54 and photo detector 56 act to focus an image of the cylinder wall at 47 onto the photo detector 56 so that an image of the 5 micron diameter spot 47 is focused thereon.

Figure 3:
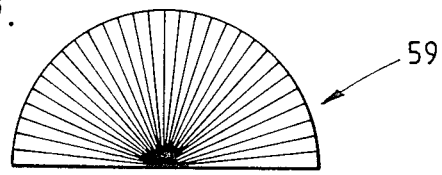
FIG. 3 is an enlarged alternative view of another part of the apparatus in FIG. 1.

The beam splitter 54 splits off the infra red beam at right angles through a lens 58 and passes the beam to a radial element detector array 59, a front view of which is shown in FIG. 3. The image on the array 59 is a far field image of the diffraction pattern of the beam at the wall 10'.

It will be understood that in use as the probe 11 is rotated about its axis the image of the two beams on the detectors 56 and 59 would rotate in unison. This rotational movement is removed by rotation of the dove prism 53 at exactly half the angular speed of the probe (and in the same direction as the incident combined beam is rotating). Thus, the only motion of the images at the detectors 56 and 59 will be due to variations in the spot images at the cylinder wall 10'.

Signals from the detectors 56,59 are passed to a suitable computer 60 where they are processed to produce the required measurements.

In use of the apparatus above described the housing 12 is firstly moved into engagement with the cylinder bore 10; in particular the annular locating portion 13 is accurately aligned with the rim 14. The probe 11 is then extended into the cylinder bore 10 and is rotated, about its axis 19 which is coincident with the axis 19' of the cylinder bore 10.

The probe is rotated at whatever speed is desirable, which may be many thousands of revolutions per minute, typically 12000 revolutions per minute and the dove prism 53 is therefore rotated at half this speed 6000 rpm. It is intended to examine the complete wall surface of the cylinder bore 10 and so, because the spot size of the HeNe laser beam 26 on the surface is about 5 microns in diameter, during each rotation of the probe 11, it should be translated upwardly (or downwardly depending on whether the probe is withdrawn or inserted during use) motor means 15 by a distance of approximately 5 microns to provide a continuous helix scan path. If however we are only interested in larger defects then we might for example withdraw the probe by 25 microns per rotation. Thus, although the speed of movement of the probe 11 will vary depending upon the minimum defect size that is to be detected, a typical rate of movement of the probe along this axis during operation might be 5 mm per second, so that a cylinder bore of 150 mm depth would be inspected in 30 seconds.

Consider firstly the HeNe beam 26. This is brought to a focus on the cylinder bore wall 10' and variations of the distance between the probe 11 and the cylinder wall will be recorded by the detector 56 as movements. This is because if the distance between the probe and cylinder wall increases then the apparent position of the spot to the lens 51 will move to one side of its optical axis, even though the spot remains in focus because the optical axis 48 along which the incident beam is passing is at right angles to the optical axis 52 and in fact lies in the focal plane of the lens 51. This relative movement of the spot is detected by the photo detector 56 and is sufficiently accurate that it may be used to provide output signals which may be processed by the computer 60 to provide measurement of:

1. The diameter of the cylinder bore 10. (Measured by the absolute position of the image on the detector 56.)

2. The ovality of the cylinder bore 10. (Measured by variations of position of the image as the probe rotates.)

3. The straightness of the cylinder bore 10. (Measured by variations as the probe moves up or down the bore.)

4. The surface finish of the cylinder bore 10. (Measured by rapid random movement of the image.)

5. Surface defects which are effectively gross deviations of surface finish. (Measured similarly to 4.)

Under paragraphs 4 and 5 above surface defects such as scratches or pits will be recorded as changes in the distance between the probe and the cylinder wall and will be detected by movement of the focus spot on the photo sensitive detector 56.

It should be noted that the surface finish on the bore can be provided in CLA (Centre Line Average) terms.

In this way, the surface finish and the other features mentioned above can be detected.

The infra red laser beam is intended to measure the honing angle, that is the angle between those fine scratches which are caused by the honing tool moving into the bore and out of the bore. The detection of this honing angle is based on the realisation that illumination of the surface of the cylinder wall by a relatively large spot will produce a reflected beam of star shaped cross-section, the arms of the star being caused by diffraction from the honing scratches and measuring the angle between the arms of the star allows one to measure the honing angle.

FIG. 3 shows a view of the radial element detector array 59. This radial detector array 59 comprises a series of detectors arranged radially and by measurement of the particular elements of the array which receive the most infra red radiation, that is those which detect the two arms of the star, one can provide a measurement of the honing angle.

The two separate functions of measuring the distance between the probe and cylinder wall and measuring the honing angle have been dealt with by two different lasers operating at different distinct frequencies which may be readily separated. In an alternative arrangement illustrated in FIG. 4 a single laser is used with a single beam and the two measurement functions are separated by using different polarisations of that single beam.

Figure 4:
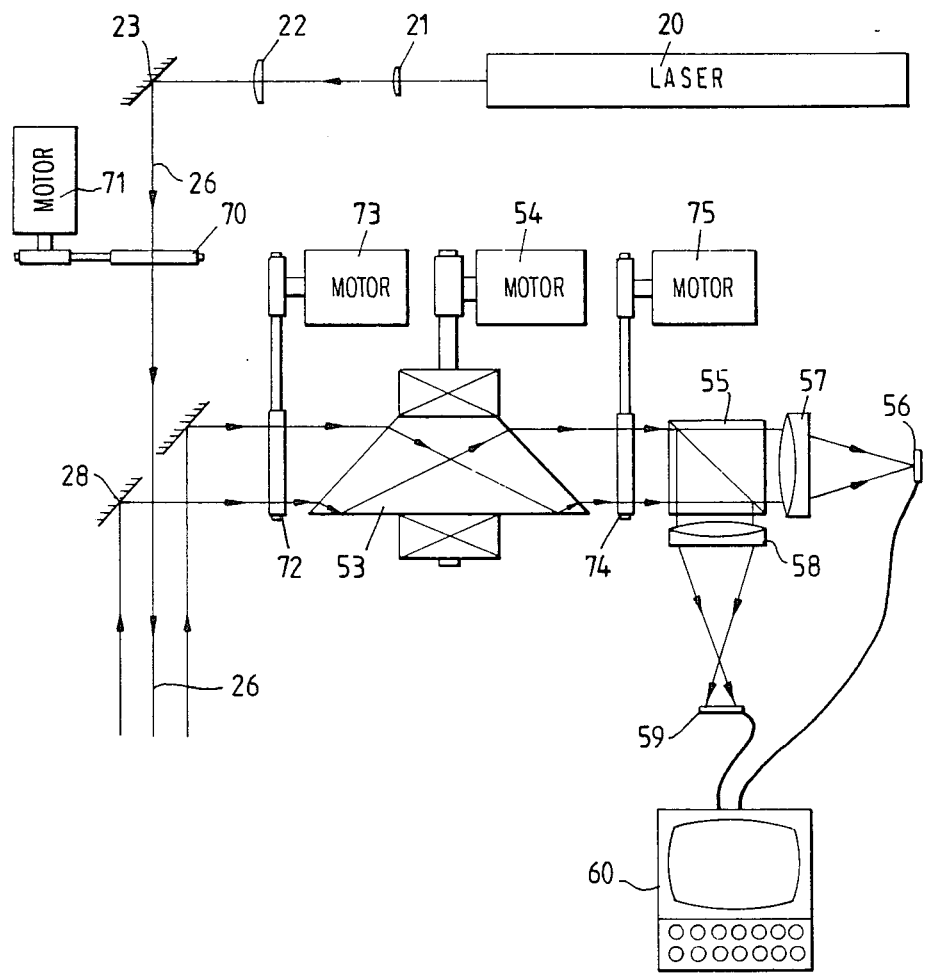
FIG. 4 shows an alternative arrangement of part of the apparatus of FIG. 1 providing a second embodiment of the invention.

Referring to FIG. 4 the laser 20 and optical components 21,22,23, and 28, 36 to 51 and 53 to 60 are retained but the laser 30 and optical components 32,33,27 are not present. Thus, there is provided a single beam 26.

Within the probe 11 the dichroic beam splitter 37 and beam combiner 43 are replaced by polarising devices. The plane mirror 28 is a dielectric mirror so as not to change the polarisation of the beam reflected therefrom.

Mounted in the beam path between the plane mirror 23 and mirror 28 is a halfwave plate 70 which is rotatable about the optical axis by means of a motor 71; between the mirror 28 and dove prism 53 there is provided a further halfwave plate 72 rotatable about the optical axis by a motor 73; and between the dove prism 53 and polarising beam splitter 55 there is provided a further halfwave plate 74 rotatable by a motor 75 about the optical axis. The motors 17,54,71,73,75 are arranged to rotate their various components as follows. If the angular velocity of rotation of the probe 11 is W, then motor 71 rotates halfwave plate 70 at W/2, motor 73 rotates halfwave plate 72 at 3 W/4, motor 54 rotates dove prism 53 at W/2, and motor 75 rotates halfwave plate 74 at W/4. (All in the same direction.)

In use the laser 20 produces a plane polarised beam. The halfwave plate 70, by its rotation rotates the plane of polarisation of the beam so that it is rotating at the same speed as the speed of rotation of the probe 11. Thus, so far as the polarising beam splitter 37 is concerned, the plane of polarisation of the incoming beam remains constant even though the beam splitter 37 itself is rotating with the probe. The relevant phase between the rotation of the halfwave plate 70 and probe 11 is arranged so that the plane of polarisation of the incident beam on the beam splitter 37 will be such (i.e., 45°) that the beam splitter will equally divide the incoming beam between the straight through path through the lens 38,39 and the reflected diverted beam through the prism 41. (We can in some circumstances change the relative phase if for some purpose we require more light to pass in one direction from the beam splitter 37 than the other.)

Reflection of the beam from the wall 10' does not affect its polarisation. The optical components in the probe 11 provide at the surface of the wall 10' two portions of the beam, one producing a five micron diameter spot and the other producing a 1 mm diameter spot.

The returning beam to the mirror 28 is thus a combined beam and is plane polarised, the plane of polarisation rotating. In order to arrange for the two beams to be collected on the two detectors, the polarisation of each must be kept separate until the beams reach the final beam splitter 55. To maintain this condition the combined beam is passed through the halfwave plate 72 after reflection at the mirror 28. This halfwave plate maintains the phase of the two beams so that they can pass through the dove prism 53 unaffected.

Rotation of the plane of polarisation of the beam emerging from the dove prism 53 is removed by the rotation of the halfwave plate 73 so that the plane of polarisation of the combined beams when reaching the beam splitter 55 is stationary.

In this way the two beam components have been provided by differently polarised beams in place of the two beams of different wavelength. That is, the beam corresponding to the first beam 26 in FIG. 1 is provided having a first plane of polarisation by passing through the beam splitter 37, and a beam corresponding to the second beam 31 of FIG. 1 is provided by means of a beam passing through the prism 41 and having a plane of polarisation at right angles to that of the other beam component. In other respects the apparatus works as in FIG. 1, that is these two beams having been produced, although they are derived from the same beam, but are simply different polarisations, are then focused and treated in a different manner so as to be separable at the beam splitter 55 when the different effects can be registered by the detectors 56 or 59.

One of the difficulties of the arrangement so far described are that with respect to the beam spot of five microns in diameter, the depth of focus is very limited (typically 25 microns) and so, the 5 microns beam spot will only remain in focus over a very short distance. Although the position sensitive detector 56 can in principle measure the position of the "centre of gravity" of the spot image thereon, it is unlikely that resolution of better than about 10% of the spot diameter could be achieved because of reflectivity changes of the surface (0.5 micron is the resolution needed to measure the surface finish). Thus, extensive variations from cylindrical form can be difficult to measure and we must maintain the axis 19 of the probe and axis 19' of the cylinder coincident to less than 25 microns.

Figure 5:
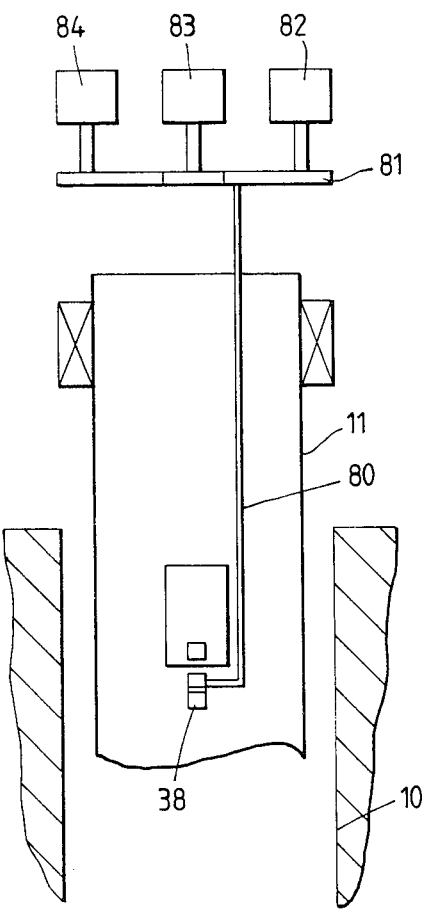
FIG. 5 shows an alternative arrangement of part of the apparatus of FIG. 1 or FIG. 4.
Figure 6:
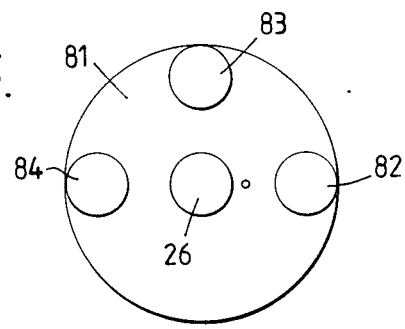
FIG. 6 is an end view of the apparatus of FIG. 5.

FIG. 5 shows an arrangement in which the 5 microns laser spot is provided by a variable focus means so that it is focused onto the cylinder wall so that greater variations of the cylinder wall from a perfect cylinder plus or minus 12 microns or greater disparity of the two axes 50 and 19 can be tolerated.

We provide a form of automatic focusing that responds relatively slowly during one revolution of the probe. In the arrangement shown in FIG. 5 the first doublet lens 38 is mounted so as to be moveable up and down with respect to the optical axis 24. The drawing is diagrammatic, but the lens 38 is mounted in a sliding bearing and is actually moved by means of a rod 80. The rod 80 passes up out through the top of the probe 11 and bears on the under surface of a non rotatable swash plate 81. The swash plate 81 is a flat plate which is normally arranged so as to be orthogonal to the optical axis 24, but which can be tilted from that orthogonal position by means of movement of actuators 82 to 84. If the swash plate is exactly orthogonal to the axis 24 then no longitudinal movement of the rod 80 takes place during rotation of the probe 11, but if the actuators 82 to 84 are actuated to tilt the swash plate out of the orthogonal position, then the rod will move up and down during each rotation of the probe to thereby move the lens 38. This changes the focal length of the telescope combination 38,39 and can be used to focus the five micron spot on the wall surface 10'.

The servo signal to operate the swash plate actuators 82 to 84 is obtained from the position sensitive detector 56. In practice the actuators 82 to 84 only need to move relatively slowly and through very small distances because it is acceptable to take several rotations of the probe to get the swash plate into the right tilt situation. It can also be used to adjust the focus so as to be able to operate with different sizes of bore.

Another way of adjusting the focus is to move the lens 38 by means of a piezoelectric actuator which either acts directly on the lens 38 or else through a lever to increase the potential movement. The piezoelectric actuator can be fed with an electrical signal produced either through a mechanical arrangement or directly by means of signals from the position detector 56.

The invention is not restricted to the details of the foregoing examples.

I claim:

1. Apparatus for measuring the distance from the apparatus to a surface comprising:
   first optical means for passing a beam of radiation to the surface at an angle other than normal,
   second optical means for viewing the area of the surface illuminated by the beam,
   means to relatively rotate the optical axis of the first optical means and the surface so that the illuminated area is moved across the surface,
   means to derotate the image of the illuminated area caused by said relative rotation, and
   means for measuring the movement of an image of said illuminated area with respect to the optical axis of the second optical means to thereby measure the position of the illuminated area and indicate the distance from the apparatus to the surface.

2. Apparatus as claimed in claim 1 characterized in that the cross sectional size of the beam at the surface is 5 microns.

3. Apparatus as claimed in claim 1 characterized in that the optical axis of the second optical means is at right angles to the optical axis of the first optical means wherein, when the illuminated area is at the focus of the second optical means, movement of the illuminated area due to change of distance between the apparatus and the surface will be in the focal plane of the second optical means.

4. Apparatus as claimed in claim 1 for use in the measurement of the diameter of a cylinder, characterized in that the rotation means is adapted to relatively rotate the optical axis of the first optical means and the surface and means is provided to move the optical axis substantially parallel to the axis of the cylinder so that the illuminated area is moved around the circumference of the cylinder in a continuous helix scan.

5. Apparatus as claimed in claim 4 characterized in that the rotation means relatively rotates the optical axis of the first optical means and the surface at 12,000 revolutions per minute.

6. Apparatus as claimed in claim 1 characterized in that said derotation means comprises a prism rotatable in synchronism with said relative rotation.

7. Apparatus as claimed in claim 1 for further use in the measurement of a honing mark cross hatch angle, characterized in that means is provided to examine a cross-section of a radiation reflected from the surface.

8. Apparatus as claimed in claim 7 characterized in that said beam is of generally circular cross-section, and said reflected radiation is of star-shaped cross-section, and means to measure the angle between arms of said star-shaped cross-section.

9. Apparatus as claimed in claim 8 characterized in that said means to measure the angle between the arms of the reflected radiation comprises a radial detector array.

10. Apparatus as claimed in claim 7 characterized in that the beam used for measurement of the distance from the apparatus to a surface is different from a beam formed by said reflected radiation used to measure the honing mark cross hatch angle.

11. Apparatus as claimed in claim 7 characterized in that the beam for measuring the distance from the apparatus to a surface and the beam for measuring the honing mark cross hatch angle are one in the same, the two aspects being measured by using different polarizations of the single beam.

12. Apparatus as claimed in claim 1 characterized in that the automatic focusing means is arranged so that the illuminated area is in focus across the surface at all times.

* * * * *